(12) United States Patent
Licht et al.

(10) Patent No.: US 11,426,518 B2
(45) Date of Patent: Aug. 30, 2022

(54) DRUG DELIVERY SYSTEM AND A METHOD FOR OPERATING A DRUG DELIVERY SYSTEM

(71) Applicant: Roche Diabetes Care, Inc., Indianapolis, IN (US)

(72) Inventors: Alexander Licht, Mannheim (DE); Tobias Kuhn-Ullrich, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 167 days.

(21) Appl. No.: 16/894,477

(22) Filed: Jun. 5, 2020

(65) Prior Publication Data

US 2020/0316295 A1 Oct. 8, 2020

Related U.S. Application Data

(63) Continuation of application No. PCT/EP2018/083792, filed on Dec. 6, 2018.

(30) Foreign Application Priority Data

Dec. 12, 2017 (EP) ..................................... 17206718

(51) Int. Cl.
*A61M 5/172* (2006.01)
*A61M 5/142* (2006.01)

(52) U.S. Cl.
CPC .......... *A61M 5/1723* (2013.01); *A61M 5/142* (2013.01); *A61M 2005/14208* (2013.01);
(Continued)

(58) Field of Classification Search
CPC .... A61M 2005/14208; A61M 2205/15; A61M 2205/3331; A61M 2205/3344;
(Continued)

(56) References Cited

U.S. PATENT DOCUMENTS 6,656,148 B2 12/2003 Das et al.
2008/0154188 A1 6/2008 Hochman
(Continued)

FOREIGN PATENT DOCUMENTS

EP 2 060 284 A1 5/2009
JP 2013-514834 A 5/2013
(Continued)

OTHER PUBLICATIONS

Extended European Search Report, EP 18 210 860.5, dated Mar. 6, 2019, 10 pages.
(Continued)

*Primary Examiner* — Jason E Flick
(74) *Attorney, Agent, or Firm* — Bose McKinney & Evans LLP (57) ABSTRACT

An inventive drug delivery system includes a reservoir that holds a drug to be administered. A drug applicator injects or infuses the drug, and a pump generates a flow of the drug from the reservoir to the drug applicator. A control system has a pressure sensor that measures pressure signals indicative of resistance against the flow of the drug and a processor is in communication with the pressure sensor. The control system detects with the pressure sensor a pressure signal indicative of the resistance against the flow of the drug while the drug is being administered and compares the measured pressure signal to a reference value. The control system also generates display data and provides it to an output device when the measured pressure signal exceeds the reference value. The display data includes a scheduled test reminder for a glucose level test that is communicated to an output device.

12 Claims, 5 Drawing Sheets

(52) U.S. Cl.
CPC . *A61M 2205/15* (2013.01); *A61M 2205/3331* (2013.01); *A61M 2205/3553* (2013.01); *A61M 2205/3561* (2013.01); *A61M 2205/52* (2013.01); *A61M 2205/583* (2013.01)

(58) Field of Classification Search
CPC .. A61M 2205/3553; A61 2205/3561; A61M 2205/3569; A61M 2205/52; A61M 2205/583; A61M 5/142; A61M 5/1723; A61M 5/486; A61M 5/14; A61M 2205/33; A61M 5/168; A61M 5/48
See application file for complete search history.

(56) References Cited

U.S. PATENT DOCUMENTS

| | | | |
|---|---|---|---|
| 2010/0262078 A1* | 10/2010 | Blomquist | A61M 5/16854 604/151 |
| 2011/0077493 A1 | 3/2011 | Shadforth et al. | |
| 2011/0124996 A1* | 5/2011 | Reinke | A61M 5/14248 600/365 |
| 2011/0152830 A1 | 6/2011 | Ruchti et al. | |
| 2014/0221965 A1* | 8/2014 | Regittnig | A61M 5/1723 604/504 |
| 2014/0378943 A1 | 12/2014 | Geipel | |
| 2016/0030683 A1 | 2/2016 | Taylor et al. | |
| 2017/0232204 A1 | 8/2017 | Knapp et al. | |

FOREIGN PATENT DOCUMENTS

| | | |
|---|---|---|
| JP | 2016-512144 A | 4/2016 |
| JP | 2016-517601 A | 6/2016 |

OTHER PUBLICATIONS

International Search Report and Written Opinion of the International Searching Authority, PCT/EP2018/083792, dated Jan. 22, 2019, 14 pages.

* cited by examiner

Fig. 4

DRUG DELIVERY SYSTEM AND A METHOD FOR OPERATING A DRUG DELIVERY SYSTEM

RELATED APPLICATIONS

This application is a continuation of PCT/EP2018/083792, filed Dec. 6, 2018, which claims priority to EP 17 206 718.3, filed Dec. 12, 2017, the entire disclosures of both of which are hereby incorporated herein by reference.

BACKGROUND

The present disclosure refers to a drug delivery system and a method for operating a drug delivery system.

For administering a drug to a person, a drug delivery system may be provided. For example, to keep blood glucose values within a normal range, it is well-known to administer insulin to diabetes patients. Insulin may be administered in single injections or via an insulin pump. By correctly administering insulin, the blood glucose level may be lowered fast and effectively. If an elevated blood glucose level (hyperglycemia) is not treated, acute and chronic complications may result. Therefore, it is essential to administer sufficient amounts of insulin to diabetes patients and to determine potential shortfalls as early as possible. Alternatively, Glucagon may be administered to elevate the blood glucose level.

When administering a drug to a patient's body, pressure in the delivery system used for administering the drug may rise due to tissue resistance against the flow of a fluid containing the drug, such as insulin. The resulting pressure may be referred to as tissue resistance pressure (TRP).

U.S. Publication No. 2014/0221965 A1 discloses an arrangement for administering a predetermined amount of a substance into an organism. The arrangement includes a member adapted to provide information indicative of a tissue resistance against flow of a fluid containing the substance upon administration into the tissue and a controller adapted to adjust an administration characteristic of the fluid based on the information such as to achieve an intended absorption rate of the substance.

U.S. Pat. No. 6,656,148 B2 relates to a piston-type infusion pump and a method of occlusion detection. The infusion pump includes processing circuitry for controlling the drive mechanism to infuse medication to a patient, including a sensor to track the position of the syringe plunger, thereby metering the amount of medication dispensed to the patient. The processing circuitry also includes a force sensor for providing signals indicative of the presence of occlusions along the infusion path. The operation of the drive mechanism causes delivery of medication to the patient. The force sensor is used to sense the force on the lead screw prior to the initiation of the delivery of medication.

U.S. Publication No. 2010/0262078 A1 relates to a system and a method for adjusting insulin infusion volume based on air in an infusion set tube includes inputting at least one location and length of an air bubble along the infusion set tube. An air bubble volume is determined in the infusion set tube. An insulin infusion volume is determined based on a desired insulin infusion. A determination is then made whether the desired insulin infusion would include the air bubble volume based on the inputted location and length of the air bubble. The air bubble volume is added to the insulin infusion volume to make an adjusted insulin infusion volume if the insulin infusion volume includes the air bubble.

U.S. Publication No. 2017/0232204 A1 refers to an improved systems and methods for medicine delivery, and in particular, improved insulin pen needles and related devices are provided. Smart injection devices record and transfer data including medicine level, delivered dose, dose confirmation, and dose time and date. Additional data captured may include glucose concentration, insulin level, carbohydrates ingested, stress level, exercise, blood pressure, and glucose high and low excursion events. Various means of data collection and analysis are provided and systems can identify and flag patients who require intervention. Smart sleeves and add sensing capability to standard insulin pens. Pen needles are provided with sensing capability to confirm and measure doses delivered by insulin pen. A two-part pen cap include a primary sleeve that connects to the insulin pen and an end cap that provides for capturing the time of dose delivery, and monitoring the hold time for a dose delivery after plunger movement.

U.S. Publication No. 2014/0378943 A1 discloses a method and devices for drug infusion and for storing a drug container. The methods and devices can include ambulatory infusion systems and dosing units. The dosing units can have and an inlet port for attachment to an external liquid drug container, an outlet port, a pump kernel, and a control valve.

SUMMARY

The present disclosure provides a drug delivery system and a method for operating that provide enhanced operation safety and functionality including error condition detection.

The following aspects, either alone or in combination with other aspects, may apply to at least one of the drug delivery system by having the system configured for such embodiment, for example, by having the control system configured accordingly, and the method for operating the drug delivery system.

The drug that is delivered may be insulin and/or glucagon. For example, the drug delivery system may be an insulin infusion system. The drug delivery system may be adapted for subcutaneous and/or intraperitoneal drug administration. Alternatively, the drug delivery system may be adapted for other methods of drug administration, for example intravenous drug administration. A user of the drug delivery system may be a patient using the drug delivery system for diabetes treatment and/or a healthcare professional treating a diabetes patient, for example by assisting the patient with diabetes management. Alternatively, a different drug may be delivered and the user may be a patient and/or a healthcare professional using the drug delivery system for treatment for a disease other than diabetes.

The resistance against the flow of the drug may be a tissue resistance against the flow of the drug. Alternatively, the resistance against the flow of the drug may not be a tissue resistance. For example, when a leakage occurs, the drug may leave the system without encountering a tissue resistance. In such a case, the resistance against the flow of the drug may be referred to as a leakage resistance. As a further alternative, the resistance against the flow of the drug may be a combination of different types of resistance, such as a combination of a tissue resistance and a leakage resistance.

Present use information may be provided in the drug delivery system, the present use information being indicative of a present time period of usage for a drug application device. The drug application device may be connected to a reservoir containing the drug to be administered which is administered via the drug application device. The drug application device may comprise a cannula or a hollow needle. A predetermined lifetime may be provided for the drug application device. For example, the predetermined lifetime may be provided based on a time of usage after which the probability of ineffective transportation of the drug to the blood, ineffective absorption of the drug at the site of administration, for example in subcutaneous tissue, and/or the probability of a blocking of the cannula or the hollow needle rises above a desired maximum.

The generating of the display data may comprise scheduling a test reminder for a glucose level test event, the glucose level test event scheduled for a test event time, generating display data indicative of the test reminder, and providing the display data to the output device of the drug delivery system at the test event time. For example, a user of the drug delivery system may be prompted via a display by the display data indicative of the test reminder to perform a glucose level measurement.

The test event time may be a predetermined test event time depending on the value of the measured pressure signal and/or a difference between the measured pressure signal and the reference value. The test event time may be chosen from a plurality of predetermined test event times—which may be provided, for example, in the control system—depending on the value of the measured pressure signal and/or a difference between the measured pressure and a reference value.

The following may be provided: providing reference use information indicative of a first reference time period of usage for the drug application device in the drug delivery system, comparing the present time period to the first reference time period of usage for the drug application device, and scheduling the test reminder, if the present time period is shorter than the first reference time period. For example, the first reference time period may be based on the predefined lifetime of the drug application device. In an embodiment, the first reference time period may be equal to the predefined lifetime of the drug application device. In alternative embodiments, the first reference time period may be defined by an offset from the predefined lifetime of the drug application device. For example, the first reference time period may be shorter by an offset than the predefined lifetime of the drug application device.

The generating of the display data may comprise generating first user information display data indicative of the measured pressure signal being above the reference value, and providing the first user information display data to the output device of the drug delivery system. For example, based on the first user information display data, a warning signal may be provided to the user via the output device. The warning signal may, for example, be a visual warning signal, such as a symbol on a display or flashing lights, an acoustic warning signal and/or a vibrational warning signal. Additionally or as an alternative, first user information display data may comprise the measured pressure signal, the reference value and/or the difference between the measured pressure signal and the reference value.

The method may comprise providing glucose level data indicative of a measured glucose level for a patient; providing glucose level reference data indicative of a glucose reference level for the patient; comparing the glucose level data to the glucose level reference data; generating second user information display data, if the measured glucose level is above the glucose reference level, the second user information display data indicative of a user warning signal; and providing the second user information display data to the output device of the drug delivery system. Alternatively, the second user information display data may be generated, if the measured glucose level is below the glucose reference level. Based on the second user information display data, a warning may be displayed prompting the user to check and/or replace the drug application device. For example, the user may be prompted to check whether the drug application device is placed correctly. This may, for example, comprise checking whether a cannula or a hollow needle is placed subcutaneously correctly. Alternatively or additionally, the user may be prompted to place the drug application device at a different location.

In an example in which the drug to be administered is insulin, the second user information display data is generated if the measured glucose level is above the glucose reference level and the glucose reference level for the patient may be indicative of whether insulin has been administered correctly and/or whether the insulin has had the desired effect. For example, the glucose reference level may be calculated by subtracting a minimum desired change in glucose level from a glucose level for the patient measured before administering the insulin. The minimum desired change in glucose level may, for example, be determined based on the amount of insulin that was to be administered.

In another embodiment in which the drug to be administered is glucagon, the second user information display data is generated if the measured glucose level is below the glucose reference level and the glucose reference level for the patient may be indicative of whether glucagon has been administered correctly and/or whether the glucagon has had the desired effect. For example, the glucose reference level may be calculated by adding a minimum desired change in glucose level to a glucose level for the patient measured before administering the glucagon. The minimum desired change in glucose level may, for example, be determined based on the amount of glucagon that was to be administered.

In other embodiments, parameter level data indicative of a measured level of a parameter other than glucose may be provided, the parameter level being indicative of a need for and/or an effectiveness of a drug that was or is to be administered. The parameter level data may be compared to parameter level reference data and second user information display data may be generated if the measured parameter level is above or below the parameter reference level.

The following may be provided: providing reference use information indicative of a second reference time period of usage for the drug application device in the drug delivery system; comparing the present time period to the second reference time period of usage for the drug application device; and generating at least one of the first and second user information display data, if the present time period is equal to or longer than the second reference time period.

For example, the second reference time period may be based on the predefined lifetime of the drug application device. In an embodiment, the second reference time period may be equal to the predefined lifetime of the drug application device. In alternative embodiments, the second reference time period may be defined by an offset from the predefined lifetime of the drug application device. For example, the second reference time period may be shorter by an offset than the predefined lifetime of the drug application device. In a different embodiment, the second reference time period may be longer by an offset than the predefined lifetime of the drug application device. The second reference time period may be equal to or different from the first reference time period.

Additionally, reference use information indicative of a third reference time period of usage for the drug application device may be provided in the drug delivery system. The present time period may be compared to the second reference time period of usage for the drug application device and the third reference time period of usage for the drug application device. The first user information display data may be generated if the present time period is equal to or longer than the second reference time period and the second user information display data may be generated if the present time period is equal to or longer than the third reference time period. The third reference time period may be equal to the first reference time period and/or the second reference time period.

The first reference time period, the second reference time period and/or the third reference time period may be indicative of a probability of a cause for the measured pressure signal exceeding the reference value. The generating and providing display data for user information may comprise generating and providing display data relating to a probable cause for the measured pressure signal exceeding the reference value.

The providing of the glucose level data may comprise providing glucose level data indicative of a glucose level for the patient measured by at least one of continuous glucose monitoring and non-continuous glucose monitoring. The glucose level data may be provided manually by the user, for example by direct input at the drug delivery system, such as via a keypad provided in the drug delivery system, or by data transfer to the drug delivery system via a wired and/or wireless connection. Alternatively or additionally, the glucose level data may be provided automatically, at least partially, for example via at least one of a wired connection and a wireless connection provided for data transfer of at least one of continuous monitoring data and non-continuous monitoring data from a glucose monitoring device to the drug delivery system.

Continuous monitoring data may be provided by a sensor that is a fully or partially implanted sensor for continuous glucose monitoring (CGM). In general, in the context of CGM, an analyte value or level indicative of a glucose value or level in the blood may be determined. The analyte value may be measured in an interstitial fluid. The measurement may be performed subcutaneously or in vivo. CGM may be implemented as a nearly real-time or quasi-continuous monitoring procedure frequently or automatically providing/updating analyte values without user interaction. In an alternative embodiment, analyte may be measured with a biosensor in a contact lens through the eye fluid or with a biosensor on the skin via transdermal measurement in sudor. A CGM sensor may stay in place for several days to weeks and then must be replaced.

The providing may comprise providing a drug delivery system having at least one of an infusion pen and an infusion pump.

One or more pressure signals may be detected. For example, the pressure sensor may detect several pressure signals at different times while the drug is administered. Alternatively or additionally, more than one pressure sensor may be provided, for example at different locations, each pressure sensor detecting one or more pressure signals. In embodiments in which more than one pressure signal is detected, the measured pressure signal being compared to the reference value may be determined by combining the detected pressure signals, for example by calculating a mean value.

The processing device may be adapted for signal and/or data processing. The processing device may be adapted for signal and/or data processing by software configuration and/or by hardware configuration. For example, the processing device may be adapted to process raw measuring data provided by the pressure sensor for comparing the measured pressure signal to the reference value. Alternatively or additionally, the processing device may be adapted for generating the display data. The processing device may comprise one processing unit. Alternatively, the processing device may comprise more than one processing unit. Processing units may be functionally connected, for example for data and/or signal transmission via wireless and/or wired connection. Processing units may form a single integrated processing device. Alternatively the processing device may comprise at least one processing unit provided separately from at least one further processing unit.

Components of the drug delivery system may be functionally connected, specifically for unidirectional or bidirectional data and/or signal transmission. For example, the pressure sensor may be connected to the processing device for transmitting measuring data and status information from the pressure sensor to the processing device and transmitting control signals from the processing device to the pressure sensor. Alternatively or additionally, the processing device may be connected to a pumping device for transmitting status data indicative of status information from the pumping device to the processing device and transmitting control signals from the processing device to the pumping device. The drug delivery system may be functionally connected, specifically for unidirectional or bidirectional data and/or signal transmission, to other devices. The drug delivery system may be connected to a blood glucose monitoring system, for example via a diabetes management device. The drug delivery system may be functionally connected to other devices via at least one of a wireless connection and a wired connection.

The output device may comprise a display on which the display data may be displayed. As an alternative or additionally, the output device may comprise an interface for data transmission. The interface for data transmission may be adapted for at least one of a wireless connection and a wired connection to another device. The display data may be transmitted from the output device to the other device. The other device may comprise a display on which the display data may be displayed. For example, the other device may be a mobile diabetes management system of a user.

Display data may comprise, as an alternative or additionally to visual display data, other types of signaling data, for example audio data. The display may comprise, as an alternative or additionally to means for visual display, other means for signaling, such as a loudspeaker and/or vibration means.

The reference value may be different for the detecting leakage in the drug delivery system than for the generating display data for user information and providing the display data to an output device of the drug delivery system. Alternatively, the reference value may be the same for the detecting leakage and for the generating and providing display data. Alternatively or additionally, the measured pressure signal may be compared to more than one reference value and the control system may be adapted for detecting leakage in the drug delivery system if the measured pressure signal is below a first reference value and for generating display data for user information and providing the display data to an output device of the drug delivery system if the measured pressure signal is above a second reference value.

The reference value(s) may be determined based on a combination of at least one systemic value and at least one physiological value, the systemic value being indicative of at least one parameter of the drug delivery system and the physiological value being indicative of at least one individual physiological parameter of a patient the drug is administered to. Additionally, the reference value(s) may be provided based on further values, such as procedural values, for example the amount of the drug to be administered (e.g., bolus size) and/or the administration rate, i.e., the amount per time of the drug to be administered.

Exemplary systemic values on which the reference value(s) may be based include reservoir size, reservoir shape, and length and/or diameter of the application device. For example, a systemic value may indicate a pressure indicative of normal operation of the drug delivery system of 2 kPa for a drug (e.g., insulin) bolus of 1 U (international units) and 2.4 kPa for a bolus of 25 U at an administration rate of 0.2 U/sec. An exemplary physiological value on which the reference value(s) may be based is a pressure value at which the drug absorption is decreased by a certain percentage in comparison to an individual reference absorption of the patient the drug is administered to.

The reference value(s) may be determined, at least in part, based on experimental results.

Detecting leakage in the drug delivery system may comprise generating leakage display data indicative of leakage having been detected and providing the leakage display data to the output device of the drug delivery system.

The pressure sensor and the processing device may be provided as one integrated component. As an alternative, the pressure sensor and the processing device may be provided separately.

With regard to the drug delivery system, the embodiments described above may apply mutatis mutandis.

In the drug delivery system, at least the reservoir, the drug application device, and the pumping device may be provided with one of a pen and an infusion pump system.

In another example, a method for operating a drug delivery system is provided. The method comprises: providing a drug delivery system having a control system comprising a pressure sensor adapted to measure pressure signals indicative of a resistance against a flow of a drug to be delivered and a processing device functionally connected to the pressure sensor; detecting a pressure signal indicative of the resistance against the flow of the drug while the drug is administered, by the pressure sensor; and comparing the measured pressure signal to a reference value. The control system is adapted for at least one of detecting leakage in the drug delivery system if the measured pressure signal is below the reference value, and generating display data for user information and providing the display data to an output device of the drug delivery system if the measured pressure signal is above the reference value.

According to another example, a drug delivery system is provided. The drug delivery system comprises a reservoir containing a drug to be administered; a drug application device adapted for injection or infusion of the drug; a pumping device adapted to generate a flow of the drug from the reservoir to the drug application device; and a control system, comprising a pressure sensor adapted to measure pressure signals indicative of a resistance against the flow of the drug and a processing device functionally connected to the pressure sensor. The control system is configured to detect a pressure signal indicative of the resistance against the flow of the drug while the drug is administered, by the pressure sensor; comparing the measured pressure signal to a reference value; and performing at least one of detecting leakage in the drug delivery system if the measured pressure signal is below the reference value, and generating display data for user information and providing the display data to an output device of the drug delivery system if the measured pressure signal is above the reference value.

According to a further example, a drug delivery system is provided, comprising: a reservoir containing a drug to be administered; a drug application device adapted for injection or infusion of the drug; a pumping device adapted to generate a flow of the drug from the reservoir to the drug application device; and a control system, comprising a pressure sensor adapted to measure pressure signals indicative of a resistance against the flow of the drug, and a processing device functionally connected to the pressure sensor. The control system is configured to: detect pressure signals indicative of a tissue resistance against the flow of the drug while the drug is administered by the pressure sensor; determine a tissue resistance value from the pressure signals; compare the tissue resistance value to a reference tissue resistance value; and detect leakage if the measured tissue resistance value is below the reference tissue resistance value.

In another example, a method for operating a drug delivery system is provided, the method comprising: providing a drug delivery system having a control system comprising a pressure sensor adapted to measure pressure signals indicative of a resistance against a flow of a drug to be delivered and a processing device functionally connected to the pressure sensor; detecting pressure signals indicative of the resistance against the flow of the drug by the pressure sensor; determining a tissue resistance value from the pressure signals; comparing the tissue resistance value to a reference tissue resistance value; and detecting leakage in the drug delivery system if the measured tissue resistance value is below the reference tissue resistance value.

For at least one of the drug delivery system and the for operating a drug delivery system as disclosed above, the configurations or embodiments as disclosed above may apply mutatis mutandis.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
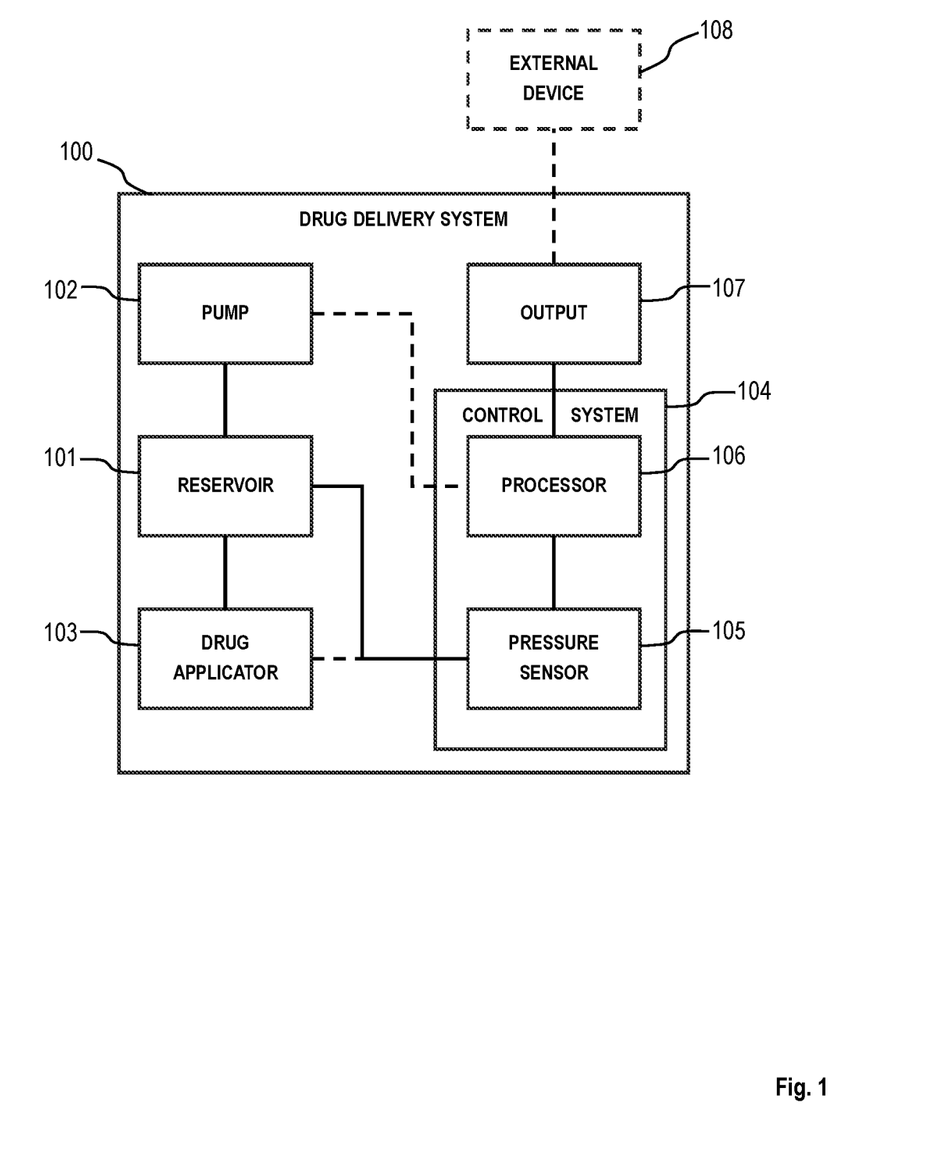
FIG. 1 is a schematic representation of a drug delivery system.

FIG. 1 shows a schematic representation of a drug delivery system 100 comprising a reservoir 101 containing a drug to be administered to a patient, a pumping device 102 (also referred to herein as a "pump") and a drug application device 103 (also referred to herein as an "applicator"). In the embodiment shown, the drug delivery system 100 is an insulin infusion system with the reservoir 101 containing insulin and the drug application device 103 being an insulin application device. In alternative embodiments, the drug delivery system 100 may be adapted to deliver a drug other than insulin, for example glucagon.

The pumping device 102 is functionally connected to the reservoir 101 such that pumping pressure exerted by the pumping device 102 generates a flow of insulin out of the reservoir 101. The pumping device 102 may include a controller to control function of the pump. Alternatively, the pumping device 102 may include a pump but no controller. In this case, the pump may be controlled by a pumping control device outside the pumping device 102. The pump may be controlled by more than one pumping control device, the pumping control devices being provided in the pumping device 102, outside of the pumping device 102, or a combination thereof.

The reservoir 101 is functionally connected to the insulin application device 103 such that the flow of insulin out of the reservoir 101 generated by the pumping device 102 exits the insulin infusion system 100 through the insulin application device 103. In the embodiment shown, the insulin application device 103 comprises a cannula. The cannula may be inserted subcutaneously into a patient's body such that insulin exiting the insulin infusion system 100 through the insulin application device 103 is administered to the patient subcutaneously. The pump in the pumping device 102 may be controlled to achieve desired administration characteristics of insulin to the patient, for example regarding an amount of insulin administered, a pressure exerted on subcutaneous tissue, and/or a flow rate of insulin.

The insulin infusion device 100 further comprises a control system 104. The control system 104 comprises a pressure sensor 105 and a processing device 106 (also referred to herein as a "processor") functionally connected to the pressure sensor 105. The pressure sensor 105 is configured to detect a pressure signal in the reservoir 101, the pressure signal being a TRP signal indicative of a tissue resistance against the flow of the insulin while the insulin is being administered. If a leak occurs, the TRP signal may be indicative of a combination of a tissue resistance against the flow of the insulin with a leakage resistance against the flow of the insulin or, if the leakage is such that no insulin is administered to the tissue, the TRP signal may be indicative of a leakage resistance against the flow of the insulin only. In a different embodiment, the pressure sensor 105 is configured to detect a TRP signal in the insulin application device 103. Alternatively, the control system 104 may comprise more than one pressure sensor 105, the pressure sensors 105 configured to detect TRP signals at different locations in the reservoir 101, the insulin application device 103, and/or at further locations in the insulin infusion system 100. For example, a first pressure sensor 105 may be configured to detect a TRP signal in the reservoir 101 proximal to the pumping device 102 and a second pressure sensor 105 may be configured to detect a TRP signal in the reservoir 101 proximal to the insulin application device 103.

The processing device 106 is configured to receive TRP signals from the pressure sensor 105 and to perform control operations as laid out in more detail below with reference to FIG. 3. The processing device 106 may further be configured to perform functions of a pumping control device to control the pump in the pumping device 102, exclusively or in addition to another pumping control device.

The insulin infusion system 100 further comprises an output device 107 (also referred to herein as an "output") functionally connected to the processing device 106. The processing device 106 is configured to generate display data and provide the display data to the output device 107. In the embodiment shown, the output device comprises a graphical display (not shown). Alternatively or additionally, the output device 107 may comprise other means of outputting signals, for example a loudspeaker and/or a vibrating means.

Figure 2:
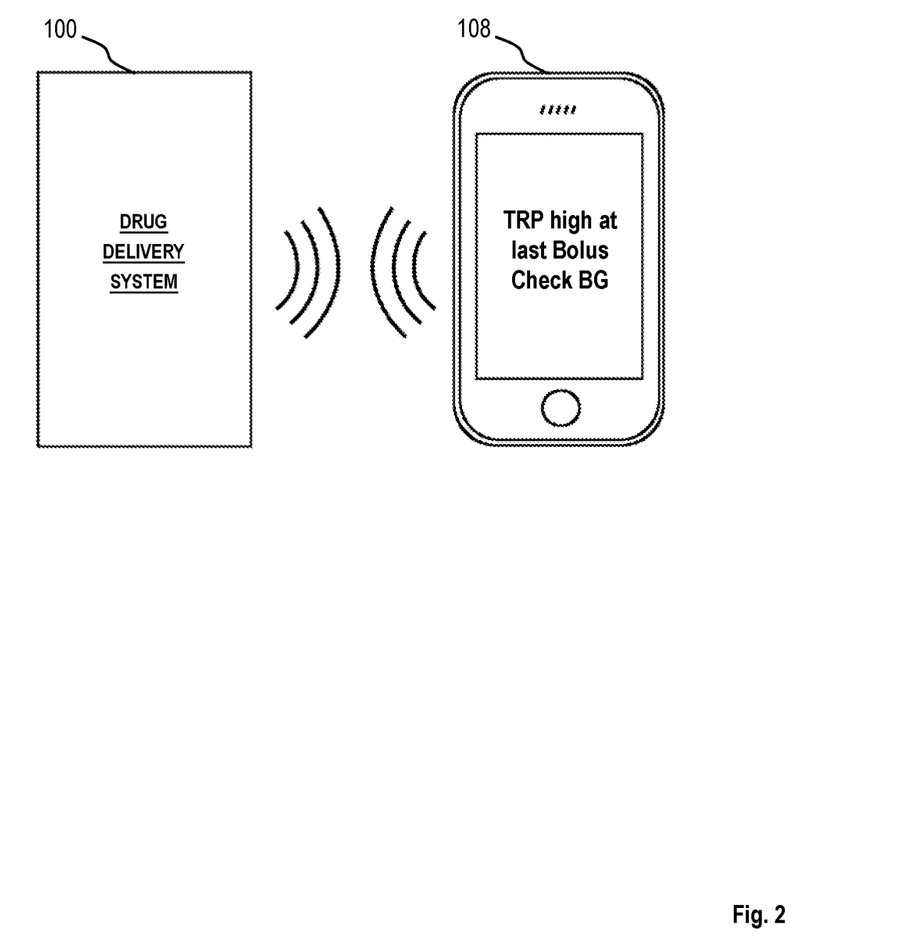
FIG. 2 is a schematic representation of a drug delivery system connected to a diabetes management device.

As a further alternative or additionally, the output device 107 may comprise an interface for data transmission via at least one of a wireless and a wired connection with an external device 108, such as a diabetes management device or a continuous glucose monitoring system. The output device may be configured for unidirectional or bidirectional data transmission with the external device 108. FIG. 2 shows a schematic representation of an insulin infusion system 100 wirelessly connected to an external device 108 which, in the embodiment shown, is a diabetes management device.

In the embodiments shown in FIGS. 1 and 2, the insulin infusion system 100 is provided with an infusion pump system. In alternative embodiments, the insulin infusion system 100 is provided with an infusion pen.

Figure 3:
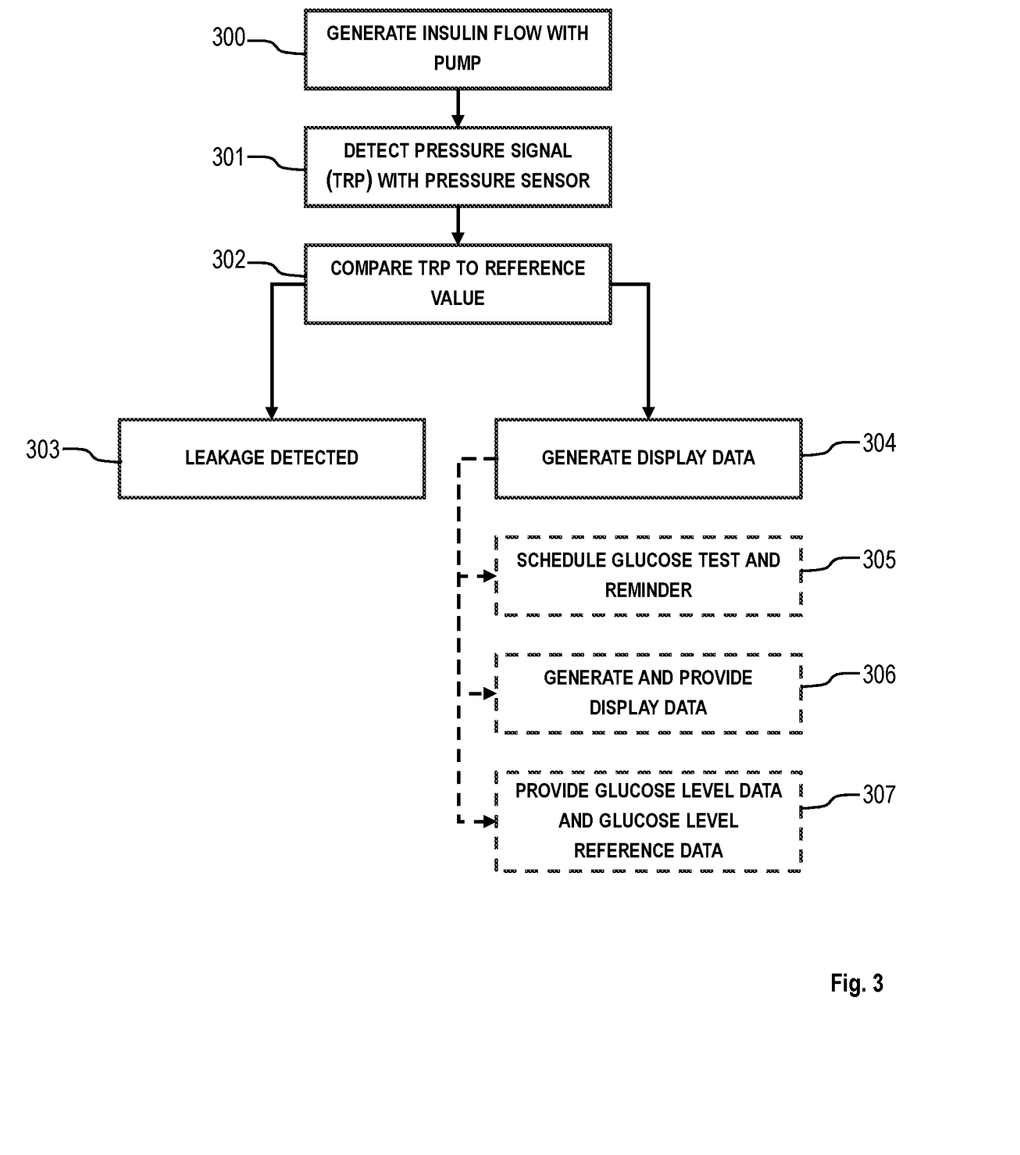
FIG. 3 is a flow diagram for steps of a method for operating a drug delivery system.

FIG. 3 shows a flow diagram for steps of a method for operating an insulin infusion system 100. In step 300, a flow of insulin to be infused from the reservoir 101 through the insulin application device 103 is generated by the pumping device 102. While the insulin is being administered, in step 301, a pressure signal indicative of the resistance against the flow of the insulin is detected by the pressure sensor 105 and the pressure signal, which may also be referred to as a TRP signal, is transmitted to the processing device 106 in the control device 104. Further, present use information indicative of a present time period of usage for the insulin application device 103, i.e., the time period for which the insulin application device 103 has been in use, may be provided in the processing device 106. Following, in step 302, the TRP signal is compared to a reference value provided in the processing device 106.

If the TRP signal is below the reference value, a leakage is detected in step 303. In the embodiment shown, leakage display data is generated by the processing device 106 and provided to the output device 107 resulting in a leakage warning being displayed in a display of the output device 107. Alternatively or additionally, leakage display data may be transmitted by the output device 107 to an external device 108, such as a diabetes management system, and the external device 108 may display a leakage warning.

If the TRP signal is above the reference value, display data is generated by the processing device 106 in step 304 and the display data is provided to the output device 107. In an embodiment, generating and providing display data by the processing device comprises step 305. In step 305, a glucose level test event is scheduled for a test event time by the processing device 106. Further, a test reminder for the glucose level test event is scheduled and display data indicative of the test reminder is generated by the processing device 106. Following, at the test time, the display data is provided to the output device 107 by the processing device 106. The test event time may depend on the measured TRP value, particularly on the difference between the measured TRP value and the reference value. For example the test event time may be determined by choosing a time interval between the TRP measurement and the test event time from a number of predetermined time intervals based on the difference between the measured TRP and the reference value.

In an embodiment, reference use information indicative of a first reference time period of usage for the insulin application device 103 is further provided in the processing device 106. The present time period is compared to the first reference time period and the test reminder is only scheduled if the present time period is shorter than the first reference time period.

In another embodiment, generating and providing display data by the processing device may comprise step 306, in addition or as an alternative to step 305. In step 306, first user information display data is created and provided to the output device 107. The first user information display data is indicative of the measured pressure signal being above the reference value, as determined in step 302. For example, at least one of a display of the output device 107 and a display of a diabetes management system connected to the insulin infusion system 100 may show a warning message stating "TRP high at last Bolus."

In a further embodiment, in addition or as an alternative to at least one of step 305 and step 306, generating and providing display data by the processing device may comprise step 307. In step 307, glucose level data indicative of a measured glucose level for the patient is provided. The glucose level for the patient may be measured by performing a single blood glucose measurement. Alternatively or additionally, continuous glucose monitoring may be used for measuring the patient's glucose level. Glucose level data may be provided by manual input of a measured glucose level by a user of the insulin infusion system 100. For data input, the insulin infusion system 100 may comprise an input device (not shown), for example a keypad or a touchscreen. Alternatively or additionally, glucose level data may be provided by automatically transferring data to the insulin infusion system 100. For automatic data transfer, the insulin infusion system 100 may be connected, via a wire or wirelessly, to an external device 108, in this case for example a continuous glucose monitoring device.

Further, glucose level reference data is provided in step 307. Glucose level reference data is indicative of a glucose level reference for the patient. The glucose level reference may be a maximum glucose level that is desired for the patient taking into account the insulin dose administered in step 300 and a time that has passed between administration of the insulin and measurement of the patient's blood glucose level. The glucose level data is compared to the glucose level reference data. If, based on this comparison, it is determined that the measured blood glucose is above the glucose reference level, second user information display data is generated and provided to the output device 107 of the insulin infusion system 100. The second user information display data is indicative of a user warning signal. For example, at least one of a display of the output device 107 and a display of a diabetes management system connected to the insulin infusion system 100 may show a warning message stating "BG high." In an embodiment, as a warning, an audio signal is generated. In another embodiment, the user warning signal prompts the user to check and/or replace the insulin application device 103 when it is determined that TRP was high while administering the insulin and, based on the measured blood glucose being above the glucose reference level, that the insulin that was to be administered has not had the desired effect.

In alternative embodiments, the glucose level reference may be a minimum glucose level that is desired. For example, in embodiments in which the drug delivery system 100 is a glucagon delivery system, the glucose level reference may be a minimum glucose level that is desired for the patient taking into account the glucagon dose administered in step 300 and a time that has passed between administration of the glucagon and measurement of the patient's blood glucose level. The second user information display data may be generated and provided to the output device 107 of the insulin infusion system 100 if it is determined that the measured blood glucose is below the glucose reference level.

In an embodiment of the method for operating an insulin infusion system 100, reference use information indicative of a second reference time period of usage for the insulin application device 103 is provided in a further step (not shown) which is executed before at least one of generating the first user information display data in step 306 and generating the second user information display data in step 307. The present time period is compared to the second reference time period of usage for the insulin application device 103. The first user information display data, the second user information display data, or both are generated if the present time period is equal to or longer than the second reference time period. For example, the second reference time period may be such that after such period of usage for the insulin application device 103, the probability is high that an elevated TRP correlates to unsatisfactory absorption of insulin by the patient. Unsatisfactory insulin absorption may be due to a number of reasons such as a reduced transportation in the patient's tissue of the insulin to the blood and a clogging of the cannula.

In further embodiments, the present time period may additionally be compared to a third reference time period of usage for the insulin application device. In such embodiments, the first user information display data is generated if the present time period is equal to or longer than the second reference time period and the second user information display data is generated if the present time period is equal to or longer than the third reference time period.

In alternative embodiments, the TRP signal is compared to a first and a second reference value in step 302. A leakage is detected in step 303, if the TRP signal is below the first reference value. Display data is generated by the processing device 106 and provided to the output device 107 in step 304, if the TRP signal is above the second reference value. In embodiments, any step or combination of steps 305, 306 and 307 may be performed subsequently.

Figure 4:
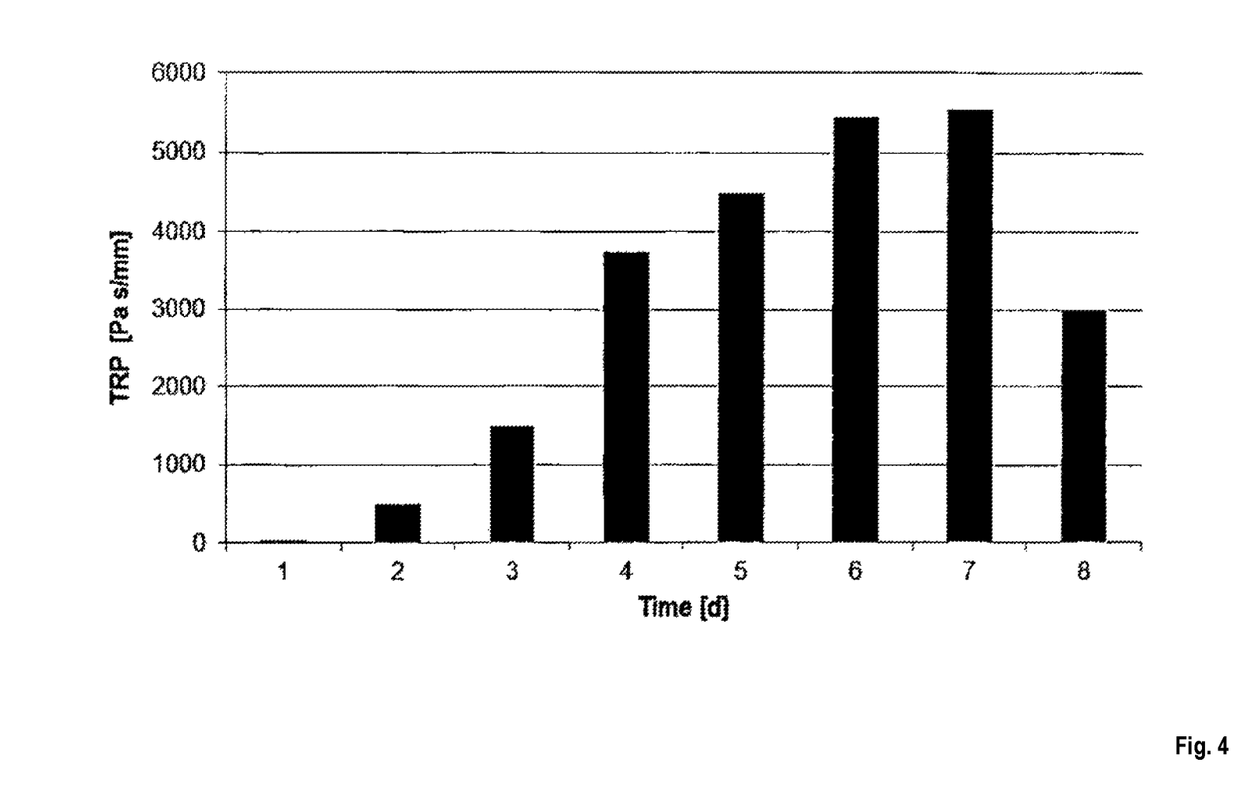
FIG. 4 is a diagram of tissue resistance pressure (TRP) during insulin administration on different days.

FIG. 4 shows exemplary results of TRP measurements according to one embodiment of the method for operating a drug delivery system 100, which in the embodiment shown is an insulin infusion system, made during insulin administration on eight consecutive days. As can be observed in FIG. 4, the TRP rises with each day on days one to seven. On day eight, there is a significant drop in TRP in comparison to day seven. Such drop in TRP after a sequence of TRP values rising daily may be indicative of a leakage in the insulin infusion system 100, as under normal conditions, a further rise in TRP would be expected on day eight. In this embodiment, based on a reference value calculated for each day by subtracting a tolerance TRP value from the previous day's TRP value, a leakage is detected based on the results of TRP measurements shown in FIG. 4 since the measured pressure signal is below the reference value.

Figure 5:
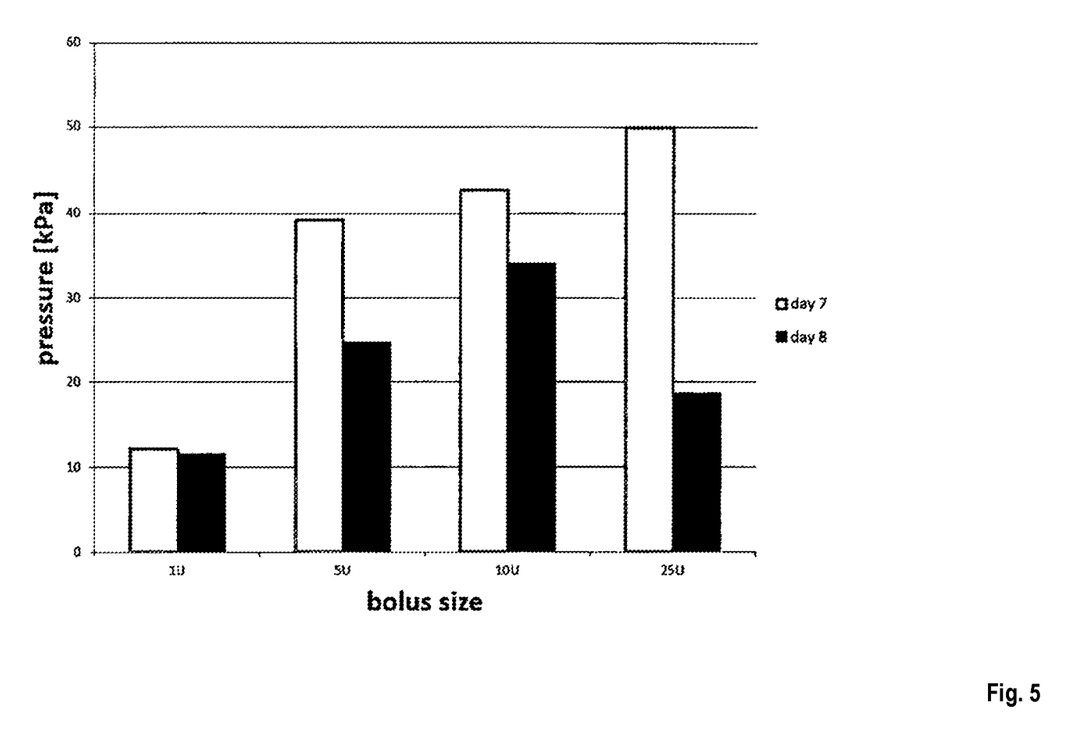
FIG. 5 is a diagram of TRP during a series of bolus administrations of insulin in the same patient on two consecutive days.

FIG. 5 shows exemplary results of TRP measurements according to a further embodiment of the method for operating a drug delivery system 100, which in the embodiment shown is an insulin infusion system. A series of bolus infusions is administered to a patient on each day in a series consecutive days. FIG. 5 shows TRP measured during bolus administrations on day seven of the series of days as empty bars and TRP measured during bolus administrations on day eight of the series of days as solid bars. It can be observed that TRP values measured on day eight are generally lower than values measured on day seven. Further, on the last measurement of day eight, a significant drop in TRP may be observed in comparison to the measurement taken directly previous. In the embodiment shown in FIG. 5, these TRP values are indicative of a loosening of the insulin application device 103 on day eight with a complete dislocation of the insulin application device between the second to last measurement and the last measurement on that day. The leakage is detected by determining that the measured pressure signal falls below a reference value determined based on previous days' measurements, in the embodiment shown.

In embodiments, such as the embodiment shown in FIG. 5, the TRP may be dependent on the volume of insulin delivered per delivery event. Therefore, the related delivery volume may be taken into account when comparing the TRP signal to the reference value or other TRP values. By way of example, multiple reference values may be defined for particular delivery volumes or a TRP measured for a certain delivery volume may be normalized and compared to a reference value for a standard delivery volume. Reference values may be predetermined and based, e.g., on the drug delivery system 100 and/or the drug application device 103 (i.e., in total the delivery system) or may be established during a predefined "run-in-time," for example the first 0.5 h, 1, 2, 3, 4, 5 or 6 hours after the patient has started to use the drug delivery system 100 or a predefined number of injections, for example using a pen, in a particular patient.

For drug delivery systems 100 adapted to deliver a drug other than insulin, the embodiments described above may apply, mutatis mutandis.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A drug delivery system, comprising:
   a reservoir configured to hold a drug;
   a drug applicator configured to inject or infuse the drug;
   a pump configured to generate a flow of the drug from the reservoir to the drug applicator; and
   a control system comprising a pressure sensor configured to measure pressure signals indicative of resistance against the flow of the drug and a processor in communication with the pressure sensor;
   wherein the control system is configured to:
      detect with the pressure sensor a pressure signal indicative of the resistance against the flow of the drug while the drug is administered;
      compare the measured pressure signal to a reference value; and
      generate display data and provide the display data to an output device when the measured pressure signal is above the reference value, the generating of display data further comprising:
         scheduling a test reminder for a glucose level test event scheduled for a test event time;
         generating display data indicative of the test reminder; and
         providing the display data to the output device at the test event time.

2. The system according to claim 1, wherein the control system is further configured to provide present use information indicative of a present time period of usage for a drug application device.

3. The system according to claim 2, wherein the control system is further configured to:
   provide reference use information indicative of a first reference time period of usage for the drug applicator;
   compare the present time period to the first reference time period; and
   schedule the test reminder when the present time period is shorter than the first reference time period.

4. The system according to claim 3, wherein the control system is further configured to:
   generate first information display data indicative of the measured pressure signal being above the reference value; and
   provide the first information display data to the output device.

5. The system according to claim 4, wherein the control system is further configured to:
   provide glucose level data indicative of a measured glucose level for a patient;
   provide glucose level reference data indicative of a glucose reference level for the patient;
   compare the glucose level data to the glucose level reference data;
   generate second information display data when the measured glucose level is above the glucose reference level, the second information display data indicative of a user warning signal; and
   provide the second information display data to the output device.

6. The system according to claim 5, wherein the control system is further configured to:
   provide reference use information indicative of a second reference time period of usage for the drug applicator;
   compare the present time period to the second reference time period of usage for the drug applicator; and
   generate at least one of the first and second information display data when the present time period is equal to or longer than the second reference time period.

7. The system according to claim 1, wherein the control system is configured to provide glucose level data indicative of a glucose level for the patient measured by at least one of continuous glucose monitoring and non-continuous glucose monitoring.

8. The system according to claim 1, wherein the control system is configured for detecting leakage in the drug delivery system when the measured pressure signal is below the reference value.

9. The system according to claim 1, wherein at least the reservoir, the drug applicator and the pump are provided with one of a pen and an infusion pump system.

10. A method for operating a drug delivery system, comprising:
   providing a reservoir configured to hold a drug;
   providing a drug applicator configured to inject or infuse the drug;
   providing a pump configured to generate a flow of the drug from the reservoir to the drug applicator;

providing a control system having a pressure sensor and a processor in communication with the pressure sensor; and using the control system to:
   detect with the pressure sensor a pressure signal indicative of resistance against the flow of the drug while the drug is being administered;
   compare the measured pressure signal to a reference value; and
   generate display data and provide the display data to an output device when the measured pressure signal is above the reference value, the generating of display data further comprising:
      scheduling a test reminder for a glucose level test event scheduled for a test event time;
      generating display data indicative of the test reminder; and
      providing the display data to the output device at the test event time.

11. The system according to claim 1, wherein the test event time is determined by selecting one of a plurality of different predetermined time intervals as a function of the difference between the measured pressure signal and the reference value.

12. The system according to claim 8, wherein the reference value is recalculated on a daily basis by subtracting a tolerance value from the reference value of the previous day.

* * * * *